US012770001B2

(12) United States Patent
Arukhe et al.

(10) Patent No.: US 12,770,001 B2
(45) Date of Patent: Oct. 20, 2026

(54) MACHINE LEARNING METHOD TO DETECT LEAKS, CLASSIFY PIPE WELD DEFECTS, AND PREDICT PIPE FAILURE

(71) Applicant: SAUDI ARABIAN OIL COMPANY, Dhahran (SA)

(72) Inventors: James O. Arukhe, Dhahran (SA); Mohammad S. Kadem, Qatif (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 762 days.

(21) Appl. No.: 18/308,489

(22) Filed: Apr. 27, 2023

(65) Prior Publication Data

US 2024/0362475 A1 Oct. 31, 2024

(51) Int. Cl.
*G06N 3/08* (2023.01)
*G01M 3/00* (2006.01)
(Continued)

(52) U.S. Cl.
CPC ................ *G06N 3/08* (2013.01); *G01M 3/00* (2013.01); *G01N 33/2045* (2019.01); *G01N 33/207* (2019.01); *G06N 3/045* (2023.01)

(58) Field of Classification Search
CPC .......... G06N 3/08; G06N 3/045; G06N 20/10; G01M 3/00; G01N 33/2045; G01N 33/207
See application file for complete search history.

(56) References Cited

U.S. PATENT DOCUMENTS 12,442,284 B2 * 10/2025 Heidari ................ G06N 3/0442
2013/0041601 A1 * 2/2013 Dintakurti ............... E03B 7/071
702/51
(Continued)

FOREIGN PATENT DOCUMENTS

CN 109858707 A * 6/2019
CN 113268883 A * 8/2021 ............. G06N 3/006
GB 2628475 A * 9/2024 ............. G06Q 10/04

OTHER PUBLICATIONS

Zabihi, Reza, and et al. "Artificial intelligence approach to predict drag reduction in crude oil pipelines." Journal of Petroleum Science and Engineering 178 (2019): 586-593 (Year: 2019).*
(Continued)

*Primary Examiner* — Douglas Kay
(74) *Attorney, Agent, or Firm* — Osha Bergman Watanabe & Burton LLP

(57) ABSTRACT

A method to perform a maintenance operation of an equipment structure is discloses. The method includes collecting monitoring data of the equipment structure disposed in a region of interest, processing the monitoring data to generate normalized monitoring data of the equipment structure, training, based on a first historical portion of the normalized monitoring data as training data and using a machine learning algorithm, an artificial neural network (ANN) model, validating, based on a second historical portion of the normalized monitoring data as validation data, the ANN model to generate a validated ANN model, detecting, using a real time portion of the normalized monitoring data as input to the validated ANN model, an anomaly of the equipment structure, and performing, in response to detecting the anomaly, the maintenance operation of the equipment structure.

20 Claims, 5 Drawing Sheets

(51) Int. Cl.

| | |
|---|---|
| ***G01N 33/2045*** | (2019.01) |
| ***G01N 33/207*** | (2019.01) |
| ***G06N 3/045*** | (2023.01) |

(56) References Cited

U.S. PATENT DOCUMENTS

| | | | | |
|---|---|---|---|---|
| 2017/0032281 | A1* | 2/2017 | Hsu | G06Q 10/06 |
| 2021/0216852 | A1* | 7/2021 | Reece | G06N 3/08 |
| 2022/0140609 | A1* | 5/2022 | Cavness | G06Q 20/065<br>166/63 |
| 2024/0310004 | A1* | 9/2024 | Chung | F17D 5/06 |

OTHER PUBLICATIONS

Kadem, Mohammad et al., "Automated Subsea Pipeline Leak Detection Using Real-Time Downhole Gauges"; 4 Proceedings of the Offshore Technology Conference; Paper No. OTC-32132-MS; pp. 1-12; Apr. 25, 2022 (Year: 2022).*

Firmansyah, Ferry et al., "Innovation in Managing Leak Repair and Crude Oil Lifting Schedule to Respond to Pipeline Leak in Offshore Terminal System"; Proceedings of the SPE/IATMI Asia Pacific Oil & Gas Conference and Exhibition; Paper No. SPE-205574-MS; pp. 1-16; Oct. 4, 2021 (16 pages).

Kyriacou, Stylianos et al., "Pipeline Leak Detection Combining Machine Learning, Data Assimilation Approaches and Pipeline Fluid Flow Physics Models"; Proceedings of the International Petroleum Technology Conference; Paper No. IPTC-22469-EA; pp. 1-7; Feb. 21, 2022 (7 pages).

Nicholas, Ed et al., "Considering Data Coupling Distributed Temperature Sensing with Real Time Transient Modeling for Pipeline Leak Detection"; Proceedings of the PSIG Annual Meeting; Paper No. PSIG-2210; pp. 1-13; May 10, 2022 (13 pages).

Kadem, Mohammad et al., "Automated Subsea Pipeline Leak Detection Using Real-Time Downhole Gauges"; Proceedings of the Offshore Technology Conference; Paper No. OTC-32132-MS; pp. 1-12; Apr. 25, 2022 (12 pages).

Zaoui, Wissem Sfar et al., "Machine-Learning Distributed-Temperature-Sensing-Based Pipeline Leak Detection"; Proceedings of the Abu Dhabi International Petroleum Exhibition & Conference; Paper No. SPE-202905-MS; pp. 1-11; Nov. 9, 2020 (11 pages).

Zhang, Jun et al., "Review of Pipeline Leak Detection Technologies"; Proceedings of the PSIG Annual Meeting; Paper No. PSIG-1303; pp. 1-13; Apr. 16, 2023 (13 pages).

* cited by examiner

MACHINE LEARNING METHOD TO DETECT LEAKS, CLASSIFY PIPE WELD DEFECTS, AND PREDICT PIPE FAILURE

BACKGROUND

Oil and gas facilities require frequent inspection to ensure integrity of equipment structures, such as pipelines or pressure vessels. The integrity of pipelines or pressure vessels relates to pipe leaks, pipe weld defects, pipe failures, pipeline drag reduction, etc.

Machine learning is a subset of artificial intelligence (AI). In machine learning, algorithms are trained to find patterns and correlations in large training data sets and to make the best decisions and predictions based on that analysis. Artificial neural networks (ANNs) are a subset of machine learning in deep learning algorithms. The ANN includes node layers, i.e., an input layer, one or more hidden layers, and an output layer. Each node connects to another node and has an associated weight and threshold. If the output of any individual node is above the specified threshold value, that node is activated, sending data to the next layer of the network. Otherwise, no data is passed along to the next layer of the network. ANNs rely on training data to learn and improve their accuracy over time. The accuracy of the ANN models is dependent on the quality and relevance of the data used for training and testing. For example, inadequate data, or data that is not representative of real-world conditions, can result in poor ANN model performance. In another example, overfitting occurs when a ANN model is too complex and fits the training data too closely, leading to poor generalization to new data. In yet another example, ANNs can be complex and difficult to interpret, making it challenging to understand the decisions made by the algorithms and leading to reduced trust in the system. Some ANN models can be computationally intensive, making them difficult to implement in real-time applications or on resource-constrained systems. Choosing the appropriate type of ANN and its parameters can be challenging and may require significant domain expertise and experimentation. Imbalanced data, where one class of events (e.g. pipe failures) occurs much less frequently than the other classes, can result in poor ANN model performance leading to an under-representation of the minority classes.

SUMMARY

In general, in one aspect, the invention relates to a method to perform a maintenance operation of an equipment structure. The method includes collecting monitoring data of the equipment structure disposed in a region of interest, processing the monitoring data to generate normalized monitoring data of the equipment structure, training, based on a first historical portion of the normalized monitoring data as training data and using a machine learning algorithm, an artificial neural network (ANN) model, validating, based on a second historical portion of the normalized monitoring data as validation data, the ANN model to generate a validated ANN model, detecting, using a real time portion of the normalized monitoring data as input to the validated ANN model, an anomaly of the equipment structure, and performing, in response to detecting the anomaly, the maintenance operation of the equipment structure.

In general, in one aspect, the invention relates to a pipe anomaly analyzer for performing a maintenance operation of an equipment structure. The pipe anomaly analyzer includes a computer processor and memory storing instructions, when executed by the computer processor comprising functionality for collecting monitoring data of the equipment structure disposed in a region of interest, processing the monitoring data to generate normalized monitoring data of the equipment structure, training, based on a first historical portion of the normalized monitoring data as training data and using a machine learning algorithm, an artificial neural network (ANN) model, validating, based on a second historical portion of the normalized monitoring data as validation data, the ANN model to generate a validated ANN model, detecting, using a real time portion of the normalized monitoring data as input to the validated ANN model, an anomaly of the equipment structure, and performing, in response to detecting the anomaly, the maintenance operation of the equipment structure.

In general, in one aspect, the invention relates to a system that includes an equipment structure disposed in a region of interest, and a pipe anomaly analyzer comprising a computer processor and memory storing instructions, when executed by the computer processor comprising functionality for collecting monitoring data of the equipment structure disposed in the region of interest, processing the monitoring data to generate normalized monitoring data of the equipment structure, training, based on a first historical portion of the normalized monitoring data as training data and using a machine learning algorithm, an artificial neural network (ANN) model, validating, based on a second historical portion of the normalized monitoring data as validation data, the ANN model to generate a validated ANN model, detecting, using a real time portion of the normalized monitoring data as input to the validated ANN model, an anomaly of the equipment structure, and performing, in response to detecting the anomaly, a maintenance operation of the equipment structure.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (for example, first, second, third) may be used as an adjective for an element (that is, any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In general, embodiments of the disclosure include a method and system for performing a maintenance operation of an equipment structure. To perform the maintenance operation, machine learning algorithms are used to detect pipe anomalies in the equipment structure. In one or more embodiments of the invention, Fuzzy Logic (FL) and Support Vector Machine (SVM) based artificial neural networks (ANNs) are combined with Artificial Bee Colony (ABC) algorithm to detect leaks, classify pipe weld defects, and predict pipe failure in the equipment structure. In addition, the ANNs are trained through the Independent Component Analysis (ICA) algorithm to predict drag reduction in crude oil pipelines. In one or more embodiments, input variables of the ANNs include pressure and flow rates, magnetic flux leakage signals, stationary and non-stationary status, temperature, type of product, land use, and pipeline age, location and diameter.

Figure 1A:
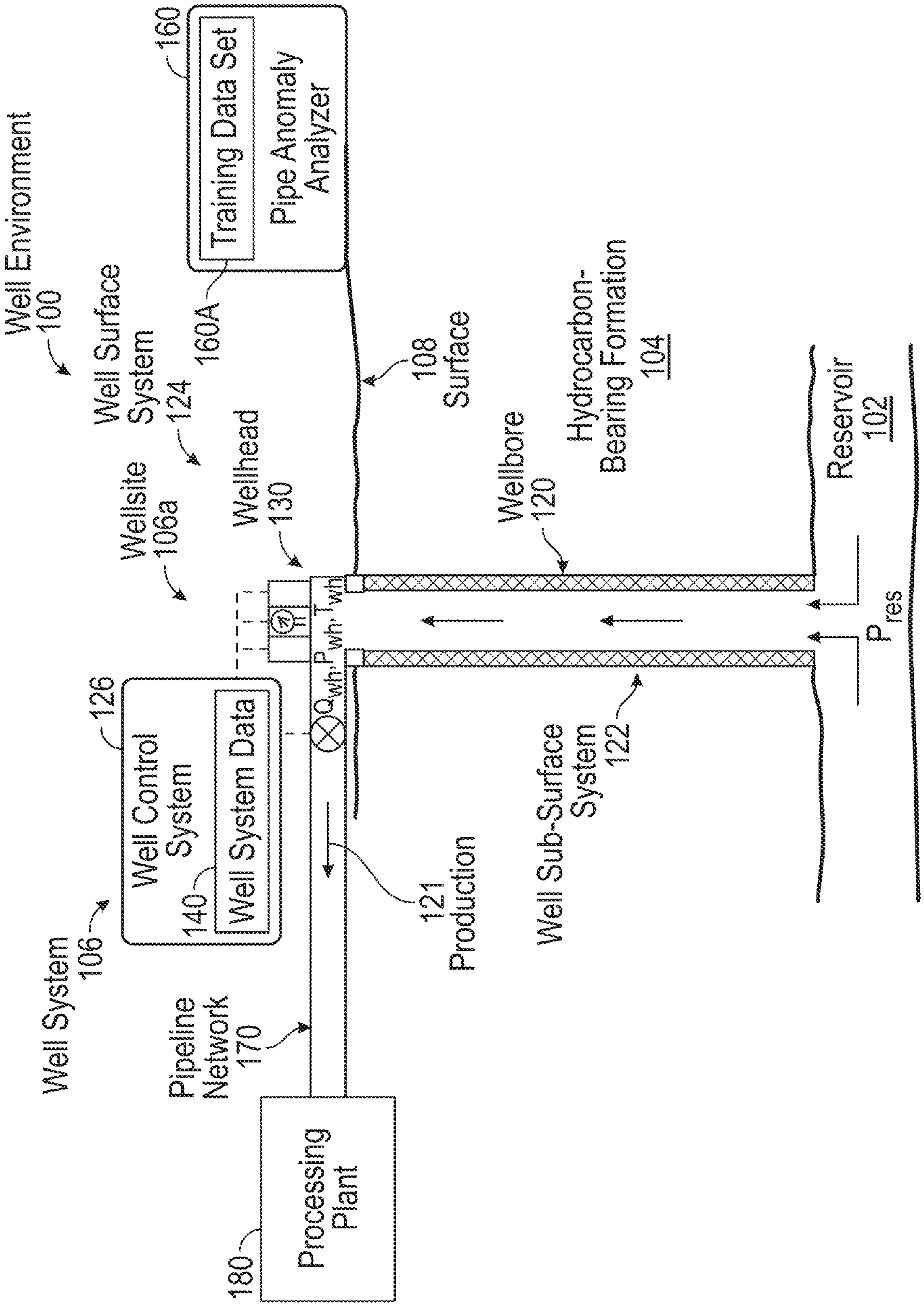
FIGS. 1A-1B show a system in accordance with one or more embodiments.

Turning to FIG. 1A, FIG. 1A shows a schematic diagram of an oil and gas facility in accordance with one or more embodiments. As shown in FIG. 1A, FIG. 1A illustrates a well environment (100) that includes a hydrocarbon reservoir ("reservoir") (102) located in a subsurface hydrocarbon-bearing formation ("formation") (104) and a well system (106). The area where the well system (106) is located is referred to as a wellsite (106*a*). The hydrocarbon-bearing formation (104) may include a porous or fractured rock formation that resides underground, beneath the earth's surface ("surface") (108). In the case of the well system (106) being a hydrocarbon well, the reservoir (102) may include a portion of the hydrocarbon-bearing formation (104). The hydrocarbon-bearing formation (104) and the reservoir (102) may include different layers of rock having varying characteristics, such as varying degrees of permeability, porosity, capillary pressure, and resistivity. In the case of the well system (106) being operated as a production well, the well system (106) may facilitate the extraction of hydrocarbons (or "production") from the reservoir (102). The well system (106) may be part of a production system that further includes a pipeline network (170) and a processing plant (180) for transporting and processing the hydrocarbons, i.e., production from the reservoir (102).

In some embodiments, the well system (106) includes a wellbore (120), a well sub-surface system (122), a well surface system (124), and a well control system ("control system") (126). The control system (126) may control various operations of the well system (106), such as well production operations, well completion operations, well maintenance operations, and reservoir monitoring, assessment and development operations. In some embodiments, the control system (126) includes a computer system.

The wellbore (120) may include a bored hole that extends from the surface (108) into a target zone of the hydrocarbon-bearing formation (104), such as the reservoir (102). An upper end of the wellbore (120), terminating at or near the surface (108), may be referred to as the "up-hole" end of the wellbore (120), and a lower end of the wellbore, terminating in the hydrocarbon-bearing formation (104), may be referred to as the "down-hole" end of the wellbore (120). The wellbore (120) may facilitate the circulation of drilling fluids during drilling operations, the flow of hydrocarbon production ("production") (121) (e.g., oil and gas) from the reservoir (102) to the surface (108) during production operations, the injection of substances (e.g., water) into the hydrocarbon-bearing formation (104) or the reservoir (102) during injection operations, or the communication of monitoring devices (e.g., logging tools) into the hydrocarbon-bearing formation (104) or the reservoir (102) during monitoring operations (e.g., during in situ logging operations).

In some embodiments, the well sub-surface system (122) includes casing installed in the wellbore (120). For example, the wellbore (120) may have a cased portion and an uncased (or "open-hole") portion. The cased portion may include a portion of the wellbore having casing (e.g., casing pipe and casing cement) disposed therein.

In some embodiments, the well surface system (124) includes a wellhead (130). The wellhead (130) may include a rigid structure installed at the "up-hole" end of the wellbore (120), at or near where the wellbore (120) terminates at the Earth's surface (108). The wellhead (130) may include structures for supporting (or "hanging") casing and production tubing extending into the wellbore (120). Production (121) may flow through the wellhead (130), after exiting the wellbore (120) and the well sub-surface system (122), including, for example, the casing and the production tubing.

In some embodiments, during operation of the well system (106), the control system (126) collects and records well system data (140) for the well system (106). The well system data (140) may include, for example, a record of measurements of wellhead pressure ($P_{wh}$) (e.g., including flowing wellhead pressure), wellhead temperature ($T_{wh}$) (e.g., including flowing wellhead temperature), wellhead production rate ($Q_{wh}$) over some or all of the life of the well system (106), and water cut data. The well system data (140) may further include pipeline monitoring data of equipment structures at the wellsite (106*a*). Throughout this disclosure, the term "equipment structure" refers to mechanical structures of equipment and piping network. In some embodiments, the measurements and monitoring data are recorded in real-time, and are available for review or use within seconds, minutes or hours of the condition being sensed (e.g., the measurements are available within 1 hour of the condition being sensed). In such an embodiment, the well system data (140) may be referred to as "real-time" well system data (140). Real-time well system data (140) may enable an operator of the well (106) to assess a relatively current state of the well system (106), and make real-time decisions regarding development and maintenance of the well system (106) and the reservoir (102), such as on-demand adjustments in regulation of production flow from the well or preventive maintenance of equipment structures to prevent disruption to the production flow from the well.

A database of recorded well system data (140), including but not limited to pipeline monitoring data, may be interrogated using machine learning and artificial intelligence techniques to identify continuous process improvement. For example, the quality of pipelines may be monitored and analyzed over a time period, or the deterioration of a pipe may be identified over time to enable proactive maintenance or repair.

In one or more embodiments, a training data set (160*a*) is generated by at least combining the recorded well system data (140), including but not limited to pipeline monitoring data, and cumulative records of pipe repair and replacement throughout a region of interest. For example, the region of interest may be a field having multiple wellsites (e.g., wellsite (106*a*)), processing plants (e.g., processing plant (180)), and pipeline networks (e.g., pipeline network (170)). In another example, the region of interest may be a portion of the field, a portion a wellsite (e.g., wellsite (106*a*)), a portion of a processing plant (e.g., processing plant (180)), or a portion of a pipeline network (e.g., pipeline network (170)). Accordingly, a machine learning algorithm for the maintenance operation of the region of interest is trained based on the training data set (160*a*). The machine learning algorithm is used to generate maintenance notices to facilitate the maintenance operation of the region of interest.

In some embodiments, the well system (106) includes a pipe anomaly analyzer (160). For example, the pipe anomaly analyzer (160) may include hardware and/or software with functionality for facilitating operations of the well system (106), such as well production operations, well drilling operation, well completion operations, well maintenance operations, and reservoir monitoring, assessment and development operations. For example, the pipe anomaly analyzer (160) may store well system data (140) such as pipeline monitoring data. In some embodiments, the pipe anomaly analyzer (160) may analyze the pipeline monitoring data to generate recommendations to facilitate various operations of the well system (106), such as a preventive maintenance of the equipment structures. In some embodiments, the pipe anomaly analyzer (160) may include hardware and/or software with functionality for generating one or more ANN models based on the training data set (160*a*) to address a range of problems, including detecting leaks, classifying pipe weld defects, and predicting pipe failures in pipelines. In addition, the pipe anomaly analyzer (160) uses ANN techniques combined with fuzzy logic, support vector machines, and artificial bee colony to effectively address various problems in pipelines. The use of ICA algorithm improves the accuracy of the predictions and helped to optimize the ANN model.

While the pipeline monitoring data is described above for equipment structures installed in the well system (106), additional and/or alternative monitoring data may correspond to equipment structures installed in the pipeline network (170), the processing plant (180), or other facilities of various industries, such as healthcare industry, agriculture, etc. For example, the pipeline monitoring data may correspond to medical imaging of tubes and branches in a human or animal body that are used for diagnosis to identify and classify diseases and conditions more accurately and efficiently. In another example, the pipeline monitoring data may correspond to pipes found in precision agriculture to facilitate identifying and classifying crop diseases, pests, and soil conditions to improve crop management and yields.

In one or more embodiments, the processing plant (180) is an industrial process plant such as an oil/petroleum refinery where petroleum (crude oil) is transformed and refined, or other types of chemical processing plants. The processing plant (180) typically includes large, sprawling industrial complexes with extensive piping network running throughout, carrying streams or liquids between large chemical processing units, such as distillation columns. Processing plant facilities require frequent inspection in order to ensure the asset integrity of the structure and safe work practices.

While the oil and gas facilities are shown as including the well environment (100) and processing plant (180), in one or more embodiments, the oil and gas facilities may additionally or alternatively include equipment (pressure vessels), storage tanks, piping and an associated pipeline network.

While the pipe anomaly analyzer (160) is shown at a well site, embodiments are contemplated where at least a portion of the pipe anomaly analyzer (160) is located away from well sites. In some embodiments, the pipe anomaly analyzer (160) may include a computer system that is similar to the computing system (400) described below with regard to FIG. 4 and the accompanying description.

Figure 1B:
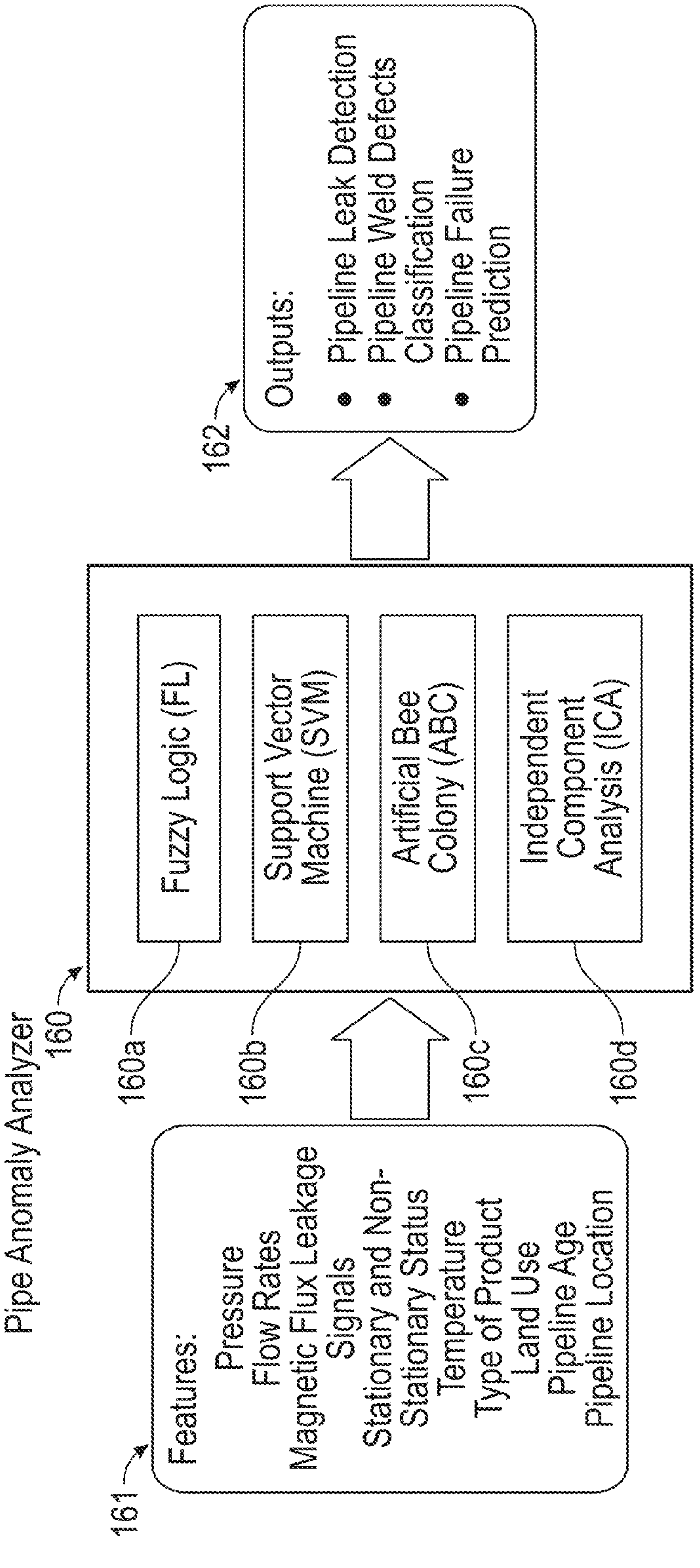

Turning to FIG. 1B, FIG. 1B illustrates an example schematic diagram of the pipe anomaly analyzer (160) depicted in FIG. 1A above. In one or more embodiments, one or more of the modules and/or elements shown in FIG. 1B may be omitted, repeated, combined and/or substituted. Accordingly, embodiments disclosed herein should not be considered limited to the specific arrangements of modules and/or elements shown in FIG. 1B.

As shown in FIG. 1B, the pipe anomaly analyzer (160) receives input data (161) that is processed using the ANNs and algorithms to generate the output results (162). The algorithms include Fuzzy Logic (FL) (160*a*), Support Vector Machine (SVM) (160*b*), Artificial Bee Colony (ABC) (160*c*), and Independent Component Analysis (ICA) (160*d*). The input data (161) includes large and diverse data sets to improve the adaptability and accuracy of the ANN models. The input data (161) is based on a common data format and data exchange protocol to ensure seamless data exchange between the pipeline management systems and the ANNs and algorithms. The data used for training the ANNs and algorithms is integrated with the data used by the pipeline management systems by using a common data storage and retrieval system and by using an integration layer that translates between the data formats used by the different systems. The input data (161) is cleaned to remove any missing or inconsistent values using techniques such as imputation, normalization, and outlier detection. The input data (161) is augmented using techniques such as random rotations, flips, and translations to generate additional data to prevent overfitting. The input data (161) is split into training data set, validation data set, and testing data set to ensure that the ANN models are trained on high-quality and relevant data.

Further as shown in FIG. 1B, the input data (161) is organized into machine learning features for input to the ANN models. Each machine learning feature is a measurable property or characteristic. Organizing input data into informative, discriminating and independent features results in effective pattern recognition, classification, and regression in machine learning. In one or more embodiments, correlation analysis, principal component analysis (PCA), recursive feature elimination (RFE), and other wrapper methods are used to select the most relevant features. Specifically, the importance of different input features is calculated and visualized, allowing for a better understanding of which features drive the decisions made by the ANNs and algorithms. As shown in FIG. 1B, the selected features include the pressure and flow rates, magnetic flux leakage signals, stationary and non-stationary status, temperature, type of product, land use, and pipeline age, location and diameter. In particular, the location of the pipeline corresponds to a position in the region of interest. For example, the location may be represented as a Cartesian coordinates, GPS coordinates, user assigned location identifiers across the field, wellsite, processing plant, or pipeline network, etc.

Further as shown in FIG. 1B, the pipe anomaly analyzer (160) includes ANNs that use or are otherwise associated with fuzzy logic (FL) (160*a*), Support Vector Machine (SVM) (160*b*), and Artificial Bee Colony (ABC) (160*c*).

In some embodiments, ANNs are used to detect leaks in pipelines by training the ANN model with historical data such as pressure readings, flow rates, and temperature variations in the training data set (160*a*) depicted in FIG. 1A above. Fuzzy logic algorithms and ANNs are combined as fuzzy neural networks (FNNs) where the FL (160*a*) is used to define the weights, from fuzzy sets, in the ANNs. FNNs are used in the pipe anomaly analyzer (160) to process the data and identify patterns that may indicate a pipe leak.

In some embodiments, ANNs are used to classify pipe weld defects by training the ANN model based on the training data set (160*a*) depicted in FIG. 1A above that stores images of pipe welds and their respective labels indicating the type of defect. Support Vector Machines (SVM) algorithms and ANNs are combined as Neural Support Vector Machines (NSVMs) where the output of the NSVM is given by the SVM (160*b*) using a central feature layer as the input. NSVMs are used in the pipe anomaly analyzer (160) to identify the hyperplane that separates the different classes of pipe weld defects. Additional techniques such as Grid Search or Random Search are also used in the pipe anomaly analyzer (160) to fine-tune the hyperparameters (e.g., learning rate, number of hidden layers, and activation functions) of the ANNs to improve the accuracy.

In some embodiments, ANNs are used to predict pipe failures by training the ANN model with historical data such as past failures, pressure and temperature readings, and corrosion rates in the training data set (160*a*) depicted in FIG. 1A above. Artificial Bee Colony (ABC) algorithms are used to optimize the ANNs and find the best combination of parameters for accurate predictions. Specifically, the ABC (160*c*) is a swarm intelligence algorithm used in the pipe anomaly analyzer (160) to optimize the training of ANNs, in particular optimizing the connection weights of feed-forward neural networks for predicting pipe failures.

In some embodiments, ANNs are used to predict drag reduction in crude oil pipelines. Independent Component Analysis (ICA) algorithms are used to separate the data into independent components, making it easier for the ANNs to learn patterns in the data of the training data set (160*a*) depicted in FIG. 1A above. The input variables for predicting drag reduction in crude oil pipelines include flow rate, pressure, temperature, viscosity, density, and composition of the crude oil. Other relevant variables such as pipeline diameter, length, and material could also be included in the training process.

In some embodiments, regularization techniques (e.g., L1 and L2 regularization) and cross-validation techniques (e.g., k-fold cross-validation) are used in the pipe anomaly analyzer (160) to assess the accuracy of the ANN models and prevent overfitting of the input data. The ANN models are simplified by reducing the number of hidden layers or neurons to speed up the processing time and simplify the ANNs and algorithms. The simplified ANNs and algorithms execute on multiple processors or GPUs thus significantly speeding up the processing time. Additional real-time data pre-processing techniques, such as feature scaling and normalization, are also used in the pipe anomaly analyzer (160) to further speed up the processing time and debottleneck in real-time processing.

In some embodiments, the ANNs and algorithms are integrated with real-time monitoring systems, allowing for real-time monitoring of the pipelines and real-time decision-making in the event of a leak or pipe failure. The ANNs and algorithms are customizable by the users by providing an interface that allows the users to modify the parameters of the ANN models and to specify the inputs and outputs of the ANN models.

In some embodiments, the ANNs and algorithms are dynamic and adaptable to changes in the pipeline systems over time. For example, techniques such as online learning may be used to allow ANN models update in real-time as new data becomes available. In another example, transfer learning techniques are used to allow the ANNs and algorithms adapt to different pipeline systems by reusing the knowledge gained from previous ANN models. These help to reduce the time and resources required to train new ANN models and improve the ANN models' accuracy.

In some embodiments, the ANNs and algorithms allow the selection of the most appropriate ANN model for a given pipeline system. For example, visualization techniques such as decision trees, rule-based ANN models, heat maps, saliency maps, and local interpretable ANN model-agnostic explanations (LIME) are used to help user to understand how the algorithms make decisions and make appropriate selections.

Based on the foregoing, the output (162) of the pipe anomaly analyzer (160) includes pipeline leak detection, pipeline weld defects classification, and pipeline failure prediction. In one or more embodiments, output results of the ANNs and algorithms are integrated with the decision-making processes of the pipeline management system. For example, the output results of the ANNs and algorithms may be translated using an integration layer of the pipeline anomaly analyzer (160) into a compatible format of the pipeline management system. A user-friendly interface allows the pipeline management systems to access the output results of the ANNs and algorithms for a user to easily understand and act upon the detected pipe anomalies.

Figure 2:
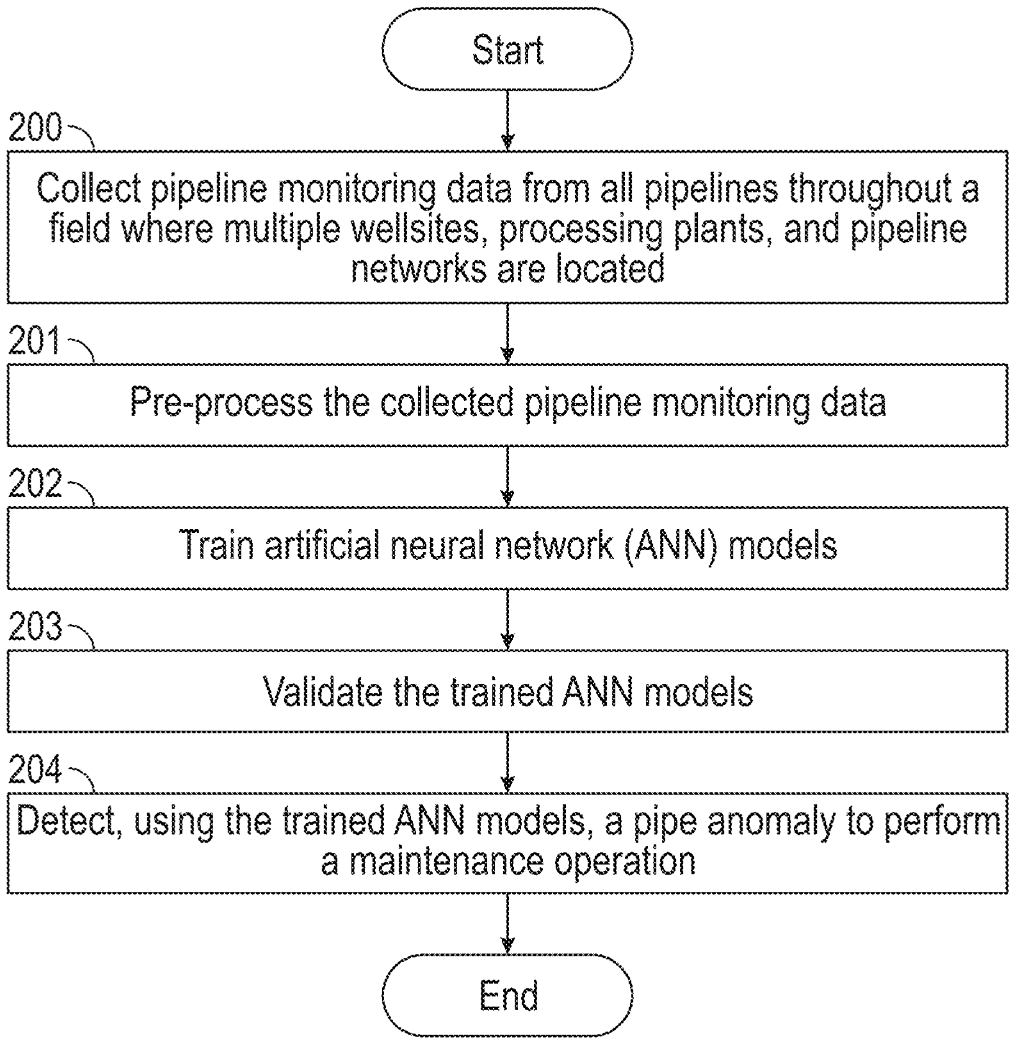
FIG. 2 shows a method flowchart in accordance with one or more embodiments.

Turning to FIG. 2, FIG. 2 shows a process flowchart in accordance with one or more embodiments. Specifically, FIG. 2 describes a method for detecting pipe anomalies. One or more blocks in FIG. 2 may be performed using one or more components as described in FIGS. 1A and 1B. While the various blocks in FIG. 2 are presented and described sequentially, one of ordinary skill in the art will appreciate that some or all of the blocks may be executed in a different order, may be combined or omitted, and some or all of the blocks may be executed in parallel and/or iteratively. Furthermore, the blocks may be performed actively or passively.

Initially in Step 200, pipeline monitoring data such as pressure readings, flow rates, temperature variations, images of pipe welds, historical failures, corrosion rates and other data related to selected features are collected from all pipelines throughout a region of interest. As noted above, the region of interest may include an entire field where multiple wellsites, processing plants, and pipeline networks are located. Alternatively, the region of interest may include a portion of the field, a portion of a wellsite, a portion of a processing plant, or a portion of a pipeline network.

In Step 201, the collected pipeline monitoring data are pre-processed to remove any missing or inconsistent values, and normalized to ensure that all variables are on the same scale.

In Step 202, ANN models are trained based on the pre-processed pipeline monitoring data using machine learning algorithms. The pipeline monitoring data includes historical monitoring data and real time monitoring data. The historical monitoring data are used as training data and validation data to train and validate the ANN models. The real time monitoring data is used as input to the ANN models to detect pipe anomalies. For example, fuzzy logic is used to train a leak detection model, SVM is used to train a pipe weld defect classification model, ABC is used to train a pipe failure prediction model, and ICA is used to train a crude oil pipeline drag reduction model.

In Step 203, the trained ANN models are evaluated on a set of validation data to assess performance and accuracy. Accordingly, the ANN models are fine-tuned based on the evaluation results to generate validated ANN models.

In Step 204, the trained ANN models are deployed in a real-world pipeline system (e.g., an equipment structure) to perform pipe anomaly detections, such as detecting leaks, classifying pipe weld defects, and predicting pipe failures. The real-world pipeline system refers to a system in active operation, such as wellbore production, fluids transportation through pipelines, online processing operation within a processing plant, etc. The ANN models take the real time monitoring data s input to generate output results of detected pipe anomalies. Accordingly, a maintenance operation is performed in response to a detected pipe anomaly. For example, the active operation of the equipment structure may be halted and a pipe with detected anomaly may be repaired or replaced in the equipment structure before re-activating the operation of the equipment structure.

Figure 3:
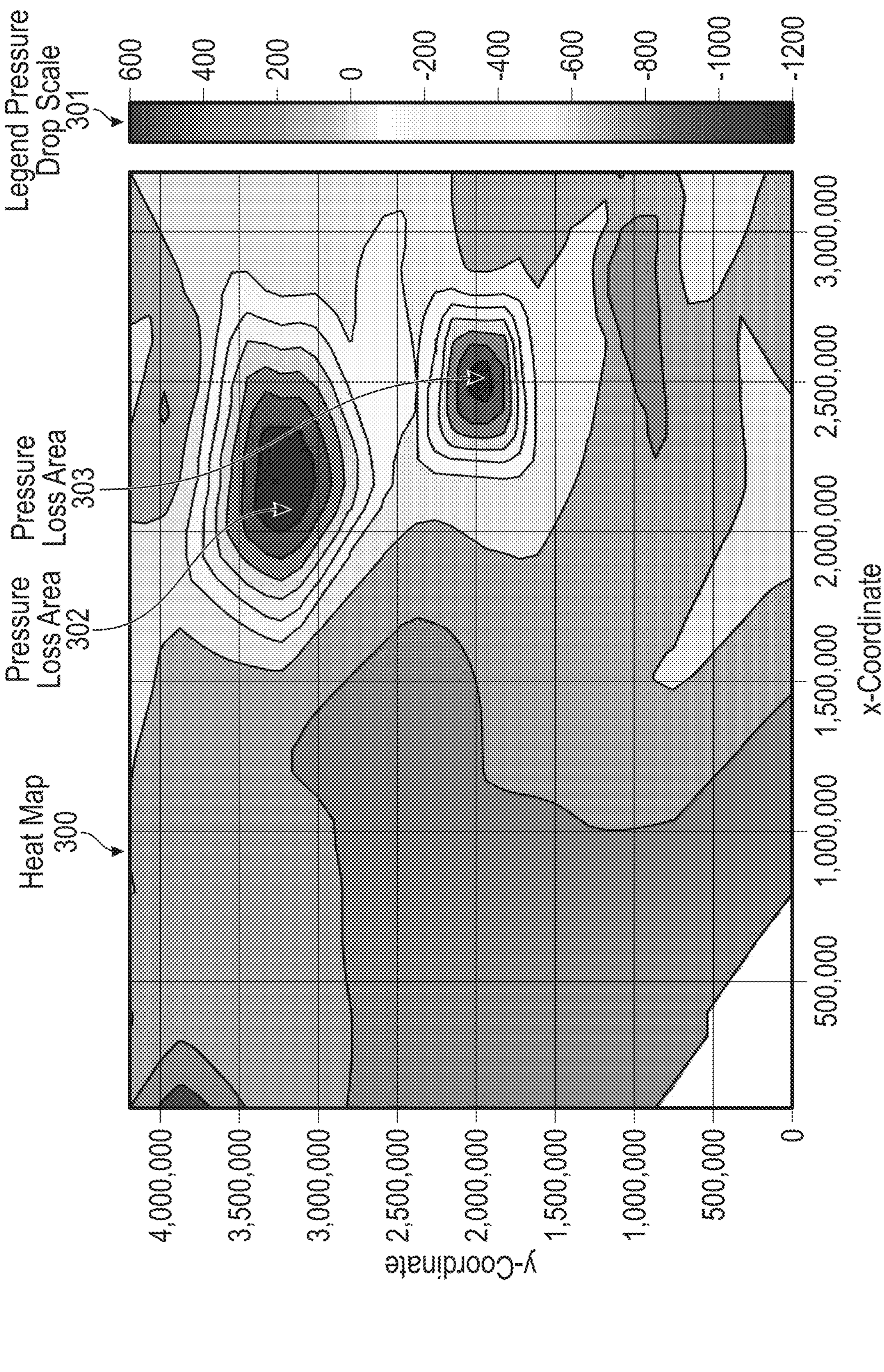
FIG. 3 shows an example in accordance with one or more embodiments.

FIG. 3 shows an example heat map (300) for detecting pipe anomalies according to the legend (301). The heat map (300) shows a pressure drop across a region of interest. As noted above, the region of interest may include an entire field where multiple wellsites, processing plants, and pipeline networks are located. Alternatively, the region of interest may include a portion of the field, a portion of a wellsite, a portion of a processing plant, or a portion of a pipeline network. For example, the heat map (300) may represent an entire field, group of wellsite with pipeline networks or a processing plant. As shown in FIG. 3, the horizontal axis represents the distance along the pipeline. The scale may be in units of kilometers, meters, or feet, depending on the location and size of the area being monitored. For example, the horizontal scale may range from 0 km to 100 km with increment at every 10 km. The vertical axis represents the pressure drop across the region of interest. The scale may be in units of psi (pounds per square inch), kPa (kilopascals), or bar, depending on the units of measurement used for pressure. For example, the vertical scale may range from 0 psi to 50 psi with increment at every 5 psi. The legend (301) represents values of pressure drop according to a grey scale where the negative pressure drop values correspond to pressure sink/loss in the reservoir of concern whereas the positive pressure drop values correspond to pressure boost. For example, the locations (302, 303) correspond to pressure loss area where detected pipeline leaks in the heat map (300) are generated using the pipe anomaly analyzer and detection method described in reference to FIGS. 1A, 1B, and 2 above.

The heat map (300) for detecting pipe anomalies is an important tool for maintaining the integrity and reliability of pipeline systems, ensuring their safe and efficient operation. For example, by monitoring the pressure drop across a pipeline, the heat map can detect anomalies such as leaks, blockages, or corrosion that could cause more significant problems if left undetected. Early detection of these anomalies allows for proactive maintenance and repair, reducing the risk of downtime, environmental damage, or safety incidents. By detecting anomalies early, the heat map can help minimize the cost of repairing pipeline issues. Proactive maintenance and repair are typically less expensive than emergency repairs and replacements that can be required if pipeline issues go undetected. By detecting pipeline issues before they escalate, the heat map can help prevent accidents, environmental damage, and human injuries. This helps to ensure that workers, communities, and the environment are protected. By identifying potential pipeline issues, the heat map can help operators optimize their pipeline systems, making them more efficient and cost-effective. This can result in improved production, reduced energy consumption, and better overall performance of the industrial process.

Figure 4:
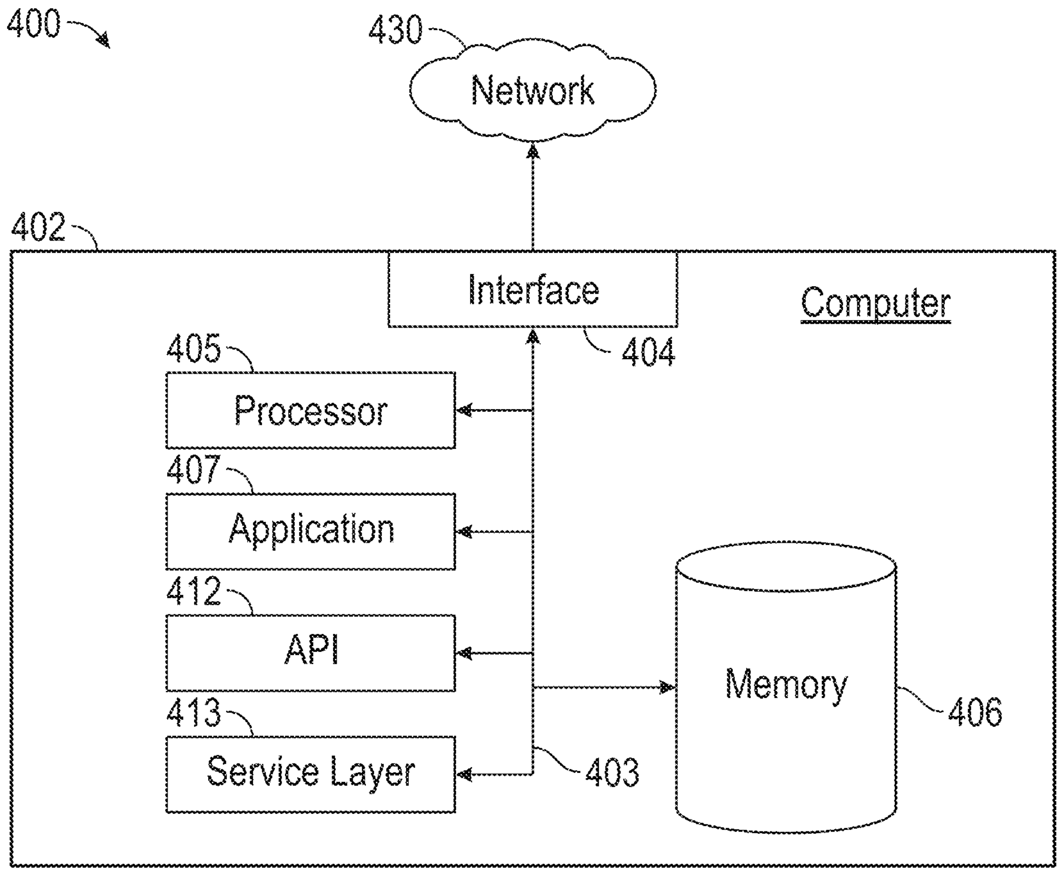
FIG. 4 shows a computing system in accordance with one or more embodiments.

Embodiments may be implemented on a computer system. FIG. 4 is a block diagram of a computer system (400) used to provide computational functionalities associated with described algorithms, methods, functions, processes, flows, and procedures as described in the instant disclosure, according to an implementation. The illustrated computer (402) is intended to encompass any computing device such as a high performance computing (HPC) device, a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (402) may include a computer that includes an input device, such as a keypad, keyboard, touch screen, or other device that can accept user information, and an output device that conveys information associated with the operation of the computer (402), including digital data, visual, or audio information (or a combination of information), or a GUI.

The computer (402) can serve in a role as a client, network component, a server, a database or other persistency, or any other component (or a combination of roles) of a computer system for performing the subject matter described in the instant disclosure. The illustrated computer (402) is communicably coupled with a network (430). In some implementations, one or more components of the computer (402) may be configured to operate within environments, including cloud-computing-based, local, global, or other environment (or a combination of environments).

At a high level, the computer (402) is an electronic computing device operable to receive, transmit, process, store, or manage data and information associated with the described subject matter. According to some implementations, the computer (402) may also include or be communicably coupled with an application server, e-mail server, web server, caching server, streaming data server, business intelligence (BI) server, or other server (or a combination of servers).

The computer (402) can receive requests over network (430) from a client application (for example, executing on another computer (402)) and responding to the received requests by processing the said requests in an appropriate software application. In addition, requests may also be sent to the computer (402) from internal users (for example, from a command console or by other appropriate access method), external or third-parties, other automated applications, as well as any other appropriate entities, individuals, systems, or computers.

Each of the components of the computer (402) can communicate using a system bus (403). In some implementations, any or all of the components of the computer (402), both hardware or software (or a combination of hardware and software), may interface with each other or the interface (404) (or a combination of both) over the system bus (403) using an application programming interface (API) (412) or a service layer (413) (or a combination of the API (412) and service layer (413). The API (412) may include specifications for routines, data structures, and object classes. The API (412) may be either computer-language independent or dependent and refer to a complete interface, a single function, or even a set of APIs. The service layer (413) provides software services to the computer (402) or other components (whether or not illustrated) that are communicably coupled to the computer (402). The functionality of the computer (402) may be accessible for all service consumers using this service layer. Software services, such as those provided by the service layer (413), provide reusable, defined business functionalities through a defined interface. For example, the interface may be software written in JAVA, C++, or other suitable language providing data in extensible markup language (XML) format or other suitable format. While illustrated as an integrated component of the computer (402), alternative implementations may illustrate the API (412) or the service layer (413) as stand-alone components in relation to other components of the computer (402) or other components (whether or not illustrated) that are communicably coupled to the computer (402). Moreover, any or all parts of the API (412) or the service layer (413) may be implemented as child or sub-modules of another software module, enterprise application, or hardware module without departing from the scope of this disclosure.

The computer (402) includes an interface (404). Although illustrated as a single interface (404) in FIG. 4, two or more interfaces (404) may be used according to particular needs, desires, or particular implementations of the computer (402). The interface (404) is used by the computer (402) for communicating with other systems in a distributed environment that are connected to the network (430). Generally, the interface (404) includes logic encoded in software or hardware (or a combination of software and hardware) and operable to communicate with the network (430). More specifically, the interface (404) may include software supporting one or more communication protocols associated with communications such that the network (430) or interface's hardware is operable to communicate physical signals within and outside of the illustrated computer (402).

The computer (402) includes at least one computer processor (405). Although illustrated as a single computer processor (405) in FIG. 4, two or more processors may be used according to particular needs, desires, or particular implementations of the computer (402). Generally, the computer processor (405) executes instructions and manipulates data to perform the operations of the computer (402) and any algorithms, methods, functions, processes, flows, and procedures as described in the instant disclosure.

The computer (402) also includes a memory (406) that holds data for the computer (402) or other components (or a combination of both) that can be connected to the network (430). For example, memory (406) can be a database storing data consistent with this disclosure. Although illustrated as a single memory (406) in FIG. 4, two or more memories may be used according to particular needs, desires, or particular implementations of the computer (402) and the described functionality. While memory (406) is illustrated as an integral component of the computer (402), in alternative implementations, memory (406) can be external to the computer (402).

The application (407) is an algorithmic software engine providing functionality according to particular needs, desires, or particular implementations of the computer (402), particularly with respect to functionality described in this disclosure. For example, application (407) can serve as one or more components, modules, applications, etc. Further, although illustrated as a single application (407), the application (407) may be implemented as multiple applications (407) on the computer (402). In addition, although illustrated as integral to the computer (402), in alternative implementations, the application (407) can be external to the computer (402).

There may be any number of computers (402) associated with, or external to, a computer system containing computer (402), each computer (402) communicating over network (430). Further, the term "client," "user," and other appropriate terminology may be used interchangeably as appropriate without departing from the scope of this disclosure. Moreover, this disclosure contemplates that many users may use one computer (402), or that one user may use multiple computers (402).

In some embodiments, the computer (402) is implemented as part of a cloud computing system. For example, a cloud computing system may include one or more remote servers along with various other cloud components, such as cloud storage units and edge servers. In particular, a cloud computing system may perform one or more computing operations without direct active management by a user device or local computer system. As such, a cloud computing system may have different functions distributed over multiple locations from a central server, which may be performed using one or more Internet connections. More specifically, cloud computing system may operate according to one or more service ANN models, such as infrastructure as a service (IaaS), platform as a service (PaaS), software as a service (SaaS), mobile "backend" as a service (MBaaS), serverless computing, artificial intelligence (AI) as a service (AIaaS), and/or function as a service (FaaS).

Embodiments provide the following advantages: (i) improved accuracy in that the techniques can be trained on high-quality and relevant data, leading to improved accuracy in detecting leaks, classifying defects, and predicting failures, (ii) real-time processing in that by optimizing the algorithms, real-time processing and decision-making can be achieved, allowing for quicker actions in the event of a leak or failure, (iii) early detection in that the ANN models can be trained to identify early signs of leaks, defects, and failures, allowing for proactive maintenance and mitigation, (iv) cost savings in that by detecting leaks, classifying defects, and predicting failures early, significant cost savings can be achieved in terms of repairs, replacements, and environmental clean-up, (v) improved safety in that by detecting and mitigating potential failures early, the safety of pipeline operations and the surrounding communities can be improved, (vi) enhanced data integration in that the algorithms can be integrated more effectively with existing pipeline management systems, allowing for seamless data exchange and decision-making, and customization in that the ANN models can be made more adaptable to different pipeline systems by incorporating more diverse data sources and allowing for greater customization of the ANN models.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed:

1. A method to perform a maintenance operation of an equipment structure, comprising:

collecting monitoring data of the equipment structure disposed in a region of interest;

processing the monitoring data to generate normalized monitoring data of the equipment structure;

training, based on a first historical portion of the normalized monitoring data as training data and using a machine learning algorithm, an artificial neural network (ANN) model;

validating, based on a second historical portion of the normalized monitoring data as validation data, the ANN model to generate a validated ANN model;

detecting, using a real time portion of the normalized monitoring data as input to the validated ANN model, an anomaly of the equipment structure;

and performing, in response to detecting the anomaly, the maintenance operation of the equipment structure;

wherein the ANN model comprises a leak detection model and the maintenance operation comprises replacing the pipe, or wherein the ANN model comprises a pipe weld defect classification model and the maintenance operation comprises repairing the pipe weld defect based on a classification generated by the pipe weld defect classification model, or wherein the ANN model comprises a pipe failure prediction model and the maintenance operation comprises a preventive maintenance of the pipe based on the failure prediction, or wherein the ANN model comprises a crude oil pipeline drag reduction model and the maintenance operation comprises optimizing transport of the crude oil pipeline.

2. The method of claim 1, wherein the region of interest comprises at least a portion of a field, and the field comprises a plurality of wellsites, a plurality of processing plants, and a plurality of pipeline networks.

3. The method of claim 1, wherein the ANN model comprises a leak detection model, wherein training the ANN model comprises using a fuzzy logic algorithm to train the leak detection model, wherein detecting the anomaly of the equipment structure comprises using the leak detection model to detect a leak in a pipe of the equipment structure, and wherein performing the maintenance operation comprises replacing the pipe.

4. The method of claim 1, wherein the ANN model comprises a pipe weld defect classification model, wherein training the ANN model comprises using a support vector machine algorithm to train the pipe weld defect classification model, wherein detecting the anomaly of the equipment structure comprises using the pipe weld defect classification model to detect and classify a pipe weld defect in a pipe of the equipment structure, and wherein performing the maintenance operation comprises repairing the pipe weld defect based on a classification generated by the pipe weld defect classification model.

5. The method of claim 1, wherein the ANN model comprises a pipe failure prediction model, wherein training the ANN model comprises using an artificial bee colony algorithm to train the pipe failure prediction model, wherein detecting the anomaly of the equipment structure comprises using the pipe failure prediction model to generate a failure prediction of a pipe of the equipment structure, and wherein performing the maintenance operation comprises a preventive maintenance of the pipe based on the failure prediction.

6. The method of claim 1, wherein the ANN model comprises a crude oil pipeline drag reduction model, wherein training the ANN model comprises using an independent component analysis algorithm to train the crude oil pipeline drag reduction model, wherein detecting the anomaly of the equipment structure comprises detecting a drag reduction in a crude oil pipeline of the equipment structure, and wherein performing the maintenance operation comprises optimizing transport of the crude oil pipeline.

7. The method of claim 1, wherein the region of interest corresponds to one of an oil and gas field, and an agriculture field.

8. A pipe anomaly analyzer for performing a maintenance operation of an equipment structure, comprising:

a computer processor;

and memory storing instructions, when executed by the computer processor comprising functionality for:

collecting monitoring data of the equipment structure disposed in a region of interest;

processing the monitoring data to generate normalized monitoring data of the equipment structure;

training, based on a first historical portion of the normalized monitoring data as training data and using a machine learning algorithm, an artificial neural network (ANN) model;

validating, based on a second historical portion of the normalized monitoring data as validation data, the ANN model to generate a validated ANN model;

detecting, using a real time portion of the normalized monitoring data as input to the validated ANN model, an anomaly of the equipment structure;

and performing, in response to detecting the anomaly, the maintenance operation of the equipment structure;

wherein the ANN model comprises a leak detection model and the maintenance operation comprises replacing the pipe, or wherein the ANN model comprises a pipe weld defect classification model and the maintenance operation comprises repairing the pipe weld defect based on a classification generated by the pipe weld defect classification model, or wherein the ANN model comprises a pipe failure prediction model and the maintenance operation comprises a preventive maintenance of the pipe based on the failure prediction, or wherein the ANN model comprises a crude oil pipeline drag reduction model and the maintenance operation comprises optimizing transport of the crude oil pipeline.

9. The pipe anomaly analyzer of claim 8, wherein the region of interest comprises at least a portion of a field, and the field comprises a plurality of wellsites, a plurality of processing plants, and a plurality of pipeline networks.

10. The pipe anomaly analyzer of claim 8, wherein the ANN model comprises a leak detection model, wherein training the ANN model comprises using a fuzzy logic algorithm to train the leak detection model,
wherein detecting the anomaly of the equipment structure comprises using the leak detection model to detect a leak in a pipe of the equipment structure, and
wherein performing the maintenance operation comprises replacing the pipe.

11. The pipe anomaly analyzer of claim 8,
wherein the ANN model comprises a pipe weld defect classification model,
wherein training the ANN model comprises using a support vector machine algorithm to train the pipe weld defect classification model,
wherein detecting the anomaly of the equipment structure comprises using the pipe weld defect classification model to detect and classify a pipe weld defect in a pipe of the equipment structure, and
wherein performing the maintenance operation comprises repairing the pipe weld defect based on a classification generated by the pipe weld defect classification model.

12. The pipe anomaly analyzer of claim 8,
wherein the ANN model comprises a pipe failure prediction model,
wherein training the ANN model comprises using an artificial bee colony algorithm to train the pipe failure prediction model,
wherein detecting the anomaly of the equipment structure comprises using the pipe failure prediction model to generate a failure prediction of a pipe of the equipment structure, and
wherein performing the maintenance operation comprises a preventive maintenance of the pipe based on the failure prediction.

13. The pipe anomaly analyzer of claim 8,
wherein the ANN model comprises a crude oil pipeline drag reduction model,
wherein training the ANN model comprises using an independent component analysis algorithm to train the crude oil pipeline drag reduction model,
wherein detecting the anomaly of the equipment structure comprises detecting a drag reduction in a crude oil pipeline of the equipment structure, and
wherein performing the maintenance operation comprises optimizing transport of the crude oil pipeline.

14. The pipe anomaly analyzer of claim 8,
wherein the region of interest corresponds to one of an oil and gas field, and an agriculture field.

15. A system comprising:
an equipment structure disposed in a region of interest;
and a pipe anomaly analyzer comprising a computer processor and memory storing instructions, when executed by the computer processor comprising functionality for:
collecting monitoring data of the equipment structure disposed in the region of interest;
processing the monitoring data to generate normalized monitoring data of the equipment structure;
training, based on a first historical portion of the normalized monitoring data as training data and using a machine learning algorithm, an artificial neural network (ANN) model;
validating, based on a second historical portion of the normalized monitoring data as validation data, the ANN model to generate a validated ANN model;
detecting, using a real time portion of the normalized monitoring data as input to the validated ANN model, an anomaly of the equipment structure;
and performing, in response to detecting the anomaly, a maintenance operation of the equipment structure;
wherein the ANN model comprises a leak detection model and the maintenance operation comprises replacing the pipe, or
wherein the ANN model comprises a pipe weld defect classification model and the maintenance operation comprises repairing the pipe weld defect based on a classification generated by the pipe weld defect classification model, or
wherein the ANN model comprises a pipe failure prediction model and the maintenance operation comprises a preventive maintenance of the pipe based on the failure prediction, or
wherein the ANN model comprises a crude oil pipeline drag reduction model and the maintenance operation comprises optimizing transport of the crude oil pipeline.

16. The system of claim 15,
wherein the region of interest comprises at least a portion of a field, and
the field comprises a plurality of wellsites, a plurality of processing plants, and a plurality of pipeline networks.

17. The system of claim 15,
wherein the ANN model comprises a leak detection model,
wherein training the ANN model comprises using a fuzzy logic algorithm to train the leak detection model,
wherein detecting the anomaly of the equipment structure comprises using the leak detection model to detect a leak in a pipe of the equipment structure, and
wherein performing the maintenance operation comprises replacing the pipe.

18. The system of claim 15,
wherein the ANN model comprises a pipe weld defect classification model,
wherein training the ANN model comprises using a support vector machine algorithm to train the pipe weld defect classification model,
wherein detecting the anomaly of the equipment structure comprises using the pipe weld defect classification model to detect and classify a pipe weld defect in a pipe of the equipment structure, and
wherein performing the maintenance operation comprises repairing the pipe weld defect based on a classification generated by the pipe weld defect classification model.

19. The system of claim 15,
wherein the ANN model comprises a pipe failure prediction model,
wherein training the ANN model comprises using an artificial bee colony algorithm to train the pipe failure prediction model,
wherein detecting the anomaly of the equipment structure comprises using the pipe failure prediction model to generate a failure prediction of a pipe of the equipment structure, and
wherein performing the maintenance operation comprises a preventive maintenance of the pipe based on the failure prediction.

20. The system of claim 15,
wherein the ANN model comprises a crude oil pipeline drag reduction model,
wherein training the ANN model comprises using an independent component analysis algorithm to train the crude oil pipeline drag reduction model, wherein detecting the anomaly of the equipment structure comprises detecting a drag reduction in a crude oil pipeline of the equipment structure, and wherein performing the maintenance operation comprises optimizing transport of the crude oil pipeline.

* * * * *